(12) United States Patent
Zott et al.

(10) Patent No.: US 12,740,747 B2
(45) **Date of Patent: *Sep. 22, 2026**

(54) DEVICE FOR DETECTING AND ILLUMINATING THE VASCULATURE USING AN FPGA

(71) Applicant: AccuVein Inc., Medford, NY (US)

(72) Inventors: Joseph Zott, Menlo Park, CA (US); Fred Wood, Medford, NY (US); Dmitriy Yavid, Stony Brook, NY (US); Seung P. Kim, San Francisco, CA (US); Klaus Zietlow, Piedmont, CA (US)

(73) Assignee: AccuVein Inc., Medford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/439,637

(22) Filed: Jan. 5, 2026

(65) Prior Publication Data

US 2026/0174388 A1 Jun. 25, 2026

Related U.S. Application Data

(63) Continuation of application No. 17/991,924, filed on Nov. 22, 2022, now Pat. No. 12,558,030, which is a (Continued)

(51) Int. Cl.

*A61B 5/00* (2006.01)
*A61B 90/00* (2016.01)

(Continued)

(52) U.S. Cl.

CPC ............ *A61B 5/489* (2013.01); *A61B 5/0033* (2013.01); *A61B 5/0062* (2013.01);

(Continued)

(58) Field of Classification Search

None

See application file for complete search history.

(56) References Cited

U.S. PATENT DOCUMENTS

| | | |
|---|---|---|
| 3,136,310 A | 6/1964 | Meltzer |
| 3,349,762 A | 10/1967 | Kapany |

(Continued)

FOREIGN PATENT DOCUMENTS

| | | |
|---|---|---|
| GB | 1298707 | 12/1972 |
| GB | 1507329 | 4/1978 |

(Continued)

OTHER PUBLICATIONS

Wiklof, Chris, "Display Technology Spawns Laser Camera", LaserFocusWorld, Dec. 1, 2004, vol. 40, Issue 12, PennWeil Corp., USA.

(Continued)

*Primary Examiner* — Christopher Koharski
*Assistant Examiner* — Farouk A Bruce
(74) *Attorney, Agent, or Firm* — Thomas A. O'Rourke; James Bongiorno; O'Rourke IP Law, PLLC

(57) ABSTRACT

An imager obtains and projects a vein image onto a patient and includes: an infrared laser; visible light laser; x-mirror; x-mirror driver; y-mirror; y-mirror driver; field programmable gate array (FPGA); photodiode; and front end circuit. The FPGA controls the lasers, x-mirror driver, and y-mirror driver to control the x-mirror and y-mirror to scan the light, and receives feedback of a state of the lasers, forming a closed control loop. The photodiode converts the reflected infrared vein image into an analog signal, which is processed by the FPGA including: performing an X-direction sum of pixel data for a plurality of boundary windows and placing it into an X-sum buffer, performing a Y-direction sum of pixel data and placing it into a Y-sum buffer, and using a total (Continued)

sum generator to obtain box filter output for each of the plurality of windows, being the X-sum buffer added to the Y-sum buffer.

4 Claims, 8 Drawing Sheets

Related U.S. Application Data continuation of application No. 16/789,459, filed on Feb. 13, 2020, now Pat. No. 11,510,617, which is a continuation of application No. 15/679,277, filed on Aug. 17, 2017, now Pat. No. 10,568,518, which is a continuation of application No. 14/723,674, filed on May 28, 2015, now Pat. No. 9,782,079, which is a continuation of application No. 13/957,767, filed on Aug. 2, 2013, now Pat. No. 9,072,426.

(60) Provisional application No. 61/678,726, filed on Aug. 2, 2012.

(51) Int. Cl.
*A61M 5/42* (2006.01)
*G02B 26/10* (2006.01)

(52) U.S. Cl.
CPC ............ *A61B 5/0082* (2013.01); *A61B 5/743* (2013.01); *A61B 2090/366* (2016.02); *A61M 5/427* (2013.01); *G02B 26/101* (2013.01)

(56) References Cited

U.S. PATENT DOCUMENTS 3,511,227 A 5/1970 Johnson
3,527,932 A 9/1970 Thomas
3,818,129 A 6/1974 Yamamoto
3,984,629 A 10/1976 Gorog
4,030,209 A 6/1977 Dreiding
4,057,784 A 11/1977 Tafoya
4,109,647 A 8/1978 Stern et al.
4,162,405 A 7/1979 Chance et al.
4,182,322 A 1/1980 Miller
4,185,808 A 1/1980 Donohoe et al.
4,213,678 A 7/1980 Pomerantzeff et al.
4,265,227 A 5/1981 Ruge
4,312,357 A 1/1982 Anderson et al.
4,315,318 A 2/1982 Kato et al.
4,321,930 A 3/1982 Jobsis et al.
4,393,366 A 7/1983 Hill
4,495,949 A 1/1985 Stoller
4,502,075 A 2/1985 DeForest et al.
4,510,938 A 4/1985 Jobsis et al.
4,536,790 A 8/1985 Kruger et al.
4,565,968 A 1/1986 Macovski
4,567,896 A 2/1986 Barnes et al.
4,576,175 A 3/1986 Epstein
4,586,190 A 4/1986 Tsuji
4,590,948 A 5/1986 Nilsson
4,596,254 A 6/1986 Adrian et al.
4,619,249 A 10/1986 Landry
4,669,467 A 6/1987 Willett et al.
4,697,147 A 9/1987 Moran et al.
4,699,149 A 10/1987 Rice
4,703,758 A 11/1987 Omura
4,766,299 A 8/1988 Tierney et al.
4,771,308 A 9/1988 Tejima et al.
4,780,919 A 11/1988 Harrison
4,799,103 A 1/1989 Muckerheide
4,817,622 A 4/1989 Pennypacker et al.
4,846,183 A 7/1989 Martin
4,861,973 A 8/1989 Hellekson et al.
4,862,894 A 9/1989 Fujii
4,899,756 A 2/1990 Sonek
4,901,019 A 2/1990 Wedeen
4,926,867 A 5/1990 Kanda et al.
RE33,234 E 6/1990 Landry
4,938,205 A 7/1990 Nudelman
5,074,642 A 12/1991 Hicks
5,088,493 A 2/1992 Giannini et al.
5,103,497 A 4/1992 Hicks
5,146,923 A 9/1992 Dhawan
5,174,298 A 12/1992 Dolfi et al.
5,184,188 A 2/1993 Bull et al.
5,214,458 A 5/1993 Kanai
5,222,495 A 6/1993 Clarke et al.
5,261,581 A 11/1993 Harden, Sr.
5,293,873 A 3/1994 Fang
5,339,817 A 8/1994 Nilsson
5,371,347 A 12/1994 Plesko
5,406,070 A 4/1995 Edgar et al.
5,418,546 A 5/1995 Nakagakiuchi et al.
5,423,091 A 6/1995 Lange
5,436,655 A 7/1995 Hiyama et al.
5,445,157 A 8/1995 Adachi et al.
D362,910 S 10/1995 Creaghan
5,485,530 A 1/1996 Lakowicz et al.
5,487,740 A 1/1996 Sulek et al.
5,494,032 A 2/1996 Robinson et al.
5,497,769 A 3/1996 Gratton et al.
5,504,316 A 4/1996 Bridgelall et al.
5,519,208 A 5/1996 Esparza et al.
5,541,820 A 7/1996 McLaughlin
5,542,421 A 8/1996 Erdman
5,598,842 A 2/1997 Ishihara et al.
5,603,328 A 2/1997 Zucker et al.
5,608,210 A 3/1997 Esparza et al.
5,610,387 A 3/1997 Bard et al.
5,625,458 A 4/1997 Alfano et al.
5,631,976 A 5/1997 Bolle et al.
5,655,530 A 8/1997 Messerschmidt
5,678,555 A 10/1997 O'Connell
5,716,796 A 2/1998 Bull et al.
5,719,399 A 2/1998 Alfano et al.
5,740,801 A 4/1998 Branson
5,747,789 A 5/1998 Godik
5,756,981 A 5/1998 Roustaei et al.
5,758,650 A 6/1998 Miller et al.
5,772,593 A 6/1998 Hakamata
5,787,185 A 7/1998 Clayden
5,814,040 A 9/1998 Nelson et al.
5,836,877 A 11/1998 Zavisian
5,847,394 A 12/1998 Alfano et al.
5,860,967 A 1/1999 Zavisian et al.
5,929,443 A 7/1999 Alfano et al.
5,946,220 A 8/1999 Lemelson
5,947,906 A 9/1999 Dawson, Jr. et al.
5,966,204 A 10/1999 Abe
5,966,230 A 10/1999 Swartz et al.
5,969,754 A 10/1999 Zeman
5,982,553 A 11/1999 Bloom et al.
5,988,817 A 11/1999 Mizushima et al.
5,995,856 A 11/1999 Manheimer et al.
5,995,866 A 11/1999 Lemelson
6,006,126 A 12/1999 Cosman
6,032,070 A 2/2000 Flock et al.
6,056,692 A 5/2000 Schwartz
6,061,583 A 5/2000 Ishihara et al.
6,083,486 A 7/2000 Weissleder et al.
6,101,036 A 8/2000 Bloom
6,113,536 A 9/2000 Aboul-Hosn et al.
6,122,042 A 9/2000 Wunderman et al.
6,132,379 A 10/2000 Patacsil et al.
6,135,599 A 10/2000 Fang
6,141,985 A 11/2000 Cluzeau et al.
6,142,650 A 11/2000 Brown et al.
6,149,061 A 11/2000 Massieu et al.
6,149,644 A 11/2000 Xie
6,171,301 B1 1/2001 Nelson et al.
6,178,340 B1 1/2001 Svetliza
6,179,260 B1 1/2001 Ohanian
6,230,046 B1 5/2001 Crane et al.
6,240,309 B1 5/2001 Yamashita et al.

(56) References Cited

U.S. PATENT DOCUMENTS 6,251,073 B1 6/2001 Imran et al.
6,263,227 B1 7/2001 Boggett et al.
6,272,376 B1 8/2001 Marcu et al.
6,301,375 B1 10/2001 Choi
6,305,804 B1 10/2001 Rice et al.
6,314,311 B1 11/2001 Williams et al.
6,334,850 B1 1/2002 Amano et al.
6,353,753 B1 3/2002 Flock et al.
6,424,858 B1 7/2002 Williams
6,436,655 B1 8/2002 Bull et al.
6,438,396 B1 8/2002 Cook et al.
6,463,309 B1 10/2002 Ilia
6,464,646 B1 10/2002 Shalom et al.
6,523,955 B1 2/2003 Eberi et al.
6,542,246 B1 4/2003 Toida
6,556,854 B1 4/2003 Sato et al.
6,556,858 B1 4/2003 Zeman
6,599,247 B1 7/2003 Stetten
6,631,286 B2 10/2003 Pfeiffer et al.
6,648,227 B2 11/2003 Swartz et al.
6,650,916 B2 11/2003 Cook et al.
6,689,075 B2 2/2004 West
6,690,964 B2 2/2004 Bieger et al.
6,702,749 B2 3/2004 Paladini et al.
6,719,257 B1 4/2004 Greene et al.
6,755,789 B2 6/2004 Stringer et al.
6,777,199 B2 8/2004 Bull et al.
6,782,161 B2 8/2004 Barolet et al.
6,845,190 B1 1/2005 Smithwick et al.
6,882,875 B1 4/2005 Crowley
6,889,075 B2 5/2005 Marchitto et al.
6,913,202 B2 7/2005 Tsikos et al.
6,923,762 B1 8/2005 Creaghan, Jr.
6,980,852 B2 12/2005 Jersey-Willuhn et al.
7,092,087 B2 8/2006 Kumar et al.
7,113,817 B1 9/2006 Winchester, Jr. et al.
7,158,660 B2 1/2007 Gee, Jr. et al.
7,158,859 B2 1/2007 Wang et al.
7,204,424 B2 4/2007 Yavid et al.
7,225,005 B2 5/2007 Kaufman et al.
7,227,611 B2 6/2007 Hull et al.
7,239,909 B2 7/2007 Zeman
7,247,832 B2 7/2007 Webb
7,280,860 B2 10/2007 Ikeda et al.
7,283,181 B2 10/2007 Allen et al.
7,302,174 B2 11/2007 Tan et al.
7,333,213 B2 2/2008 Kempe
D566,283 S 4/2008 Brafford et al.
7,359,531 B2 4/2008 Endoh et al.
7,376,456 B2 5/2008 Marshik-Geurts et al.
7,428,997 B2 9/2008 Wiklof et al.
7,431,695 B1 10/2008 Creaghan
7,448,995 B2 11/2008 Wiklof et al.
7,532,746 B2 5/2009 Marcotte et al.
7,545,837 B2 6/2009 Oka
7,559,895 B2 7/2009 Stetten et al.
7,579,592 B2 8/2009 Kaushal
7,608,057 B2 10/2009 Woehr et al.
7,699,776 B2 4/2010 Walker et al.
7,708,695 B2 5/2010 Akkermans et al.
7,792,334 B2 9/2010 Cohen et al.
7,846,103 B2 12/2010 Cannon, Jr. et al.
7,848,103 B2 12/2010 Zhan
7,904,138 B2 3/2011 Goldman et al.
7,904,139 B2 3/2011 Chance
7,925,332 B2 4/2011 Crane et al.
7,966,051 B2 6/2011 Xie et al.
7,983,738 B2 7/2011 Goldman et al.
8,032,205 B2 10/2011 Mullani
8,078,263 B2 12/2011 Zeman et al.
8,150,500 B2 4/2012 Goldman
8,187,189 B2 5/2012 Jung et al.
8,199,189 B2 6/2012 Kagenow et al.
8,244,333 B2 8/2012 Wood
8,255,040 B2 8/2012 Goldman et al.
8,320,998 B2 11/2012 Sato
8,336,839 B2 12/2012 Broccoleri et al.
8,350,847 B2 1/2013 Shpunt
8,364,246 B2 1/2013 Thierman
8,391,960 B2 3/2013 Wood et al.
8,463,364 B2 6/2013 Wood et al.
8,467,855 B2 6/2013 Yasui
8,478,386 B2 7/2013 Goldman et al.
8,480,662 B2 7/2013 Stolen et al.
8,489,178 B2 7/2013 Wood et al.
8,494,616 B2 7/2013 Zeman
8,498,694 B2 7/2013 McGuire, Jr. et al.
8,509,495 B2 8/2013 Xu et al.
8,532,727 B2 9/2013 Ali
8,537,203 B2 9/2013 Seibel et al.
8,548,572 B2 10/2013 Crane
8,594,770 B2 11/2013 Wood et al.
8,630,465 B2 1/2014 Wieringa et al.
8,649,848 B2 2/2014 Crane et al.
8,665,507 B2 3/2014 Luciano et al.
8,730,321 B2 5/2014 Luciano et al.
8,838,210 B2 9/2014 Wood et al.
9,022,940 B2 5/2015 Meier
9,072,426 B2 7/2015 Zott et al.
12,318,219 B2 6/2025 Wood et al.
2001/0006426 A1 7/2001 Son et al.
2001/0056237 A1 12/2001 Cane et al.
2002/0016533 A1 2/2002 Marchitto et al.
2002/0118338 A1 8/2002 Kohayakawa
2002/0188203 A1 12/2002 Smith et al.
2003/0018271 A1 1/2003 Kimble
2003/0037375 A1 2/2003 Riley et al.
2003/0052105 A1 3/2003 Nagano et al.
2003/0120154 A1 6/2003 Sauer et al.
2003/0125629 A1 7/2003 Usluner
2003/0156260 A1 8/2003 Putilin et al.
2004/0015062 A1 1/2004 Ntziachristos et al.
2004/0015158 A1 1/2004 Chen et al.
2004/0022421 A1 2/2004 Endoh et al.
2004/0046031 A1 3/2004 Knowles et al.
2004/0171923 A1 9/2004 Kalafut et al.
2004/0222301 A1 11/2004 Willins et al.
2004/0237051 A1 11/2004 Clauson
2005/0017924 A1 1/2005 Utt et al.
2005/0033145 A1 2/2005 Graham et al.
2005/0043596 A1 2/2005 Chance
2005/0047134 A1 3/2005 Mueller et al.
2005/0085732 A1 4/2005 Sevick-Muraca et al.
2005/0085802 A1 4/2005 Gruzdev et al.
2005/0113650 A1 5/2005 Pacione et al.
2005/0131291 A1 6/2005 Floyd et al.
2005/0135102 A1 6/2005 Gardiner et al.
2005/0141069 A1 6/2005 Wood et al.
2005/0143662 A1 6/2005 Marchitto et al.
2005/0146765 A1 7/2005 Turner et al.
2005/0154303 A1 7/2005 Walker et al.
2005/0157939 A1 7/2005 Arsenault et al.
2005/0161051 A1 7/2005 Pankratov et al.
2005/0168980 A1 8/2005 Dryden et al.
2005/0174777 A1 8/2005 Cooper et al.
2005/0175048 A1 8/2005 Stern et al.
2005/0187477 A1 8/2005 Serov et al.
2005/0215875 A1 9/2005 Khou
2005/0265586 A1 12/2005 Rowe et al.
2005/0281445 A1 12/2005 Marcotte et al.
2006/0007134 A1 1/2006 Ting
2006/0020212 A1 1/2006 Xu et al.
2006/0025679 A1 2/2006 Viswanathan et al.
2006/0052690 A1 3/2006 Sirohey et al.
2006/0081252 A1 4/2006 Wood
2006/0100523 A1 5/2006 Ogle et al.
2006/0103811 A1 5/2006 May et al.
2006/0122515 A1 6/2006 Zeman et al.
2006/0129037 A1 6/2006 Kaufman et al.
2006/0129038 A1 6/2006 Zelenchuk et al.
2006/0151449 A1 7/2006 Warner et al.
2006/0173351 A1 8/2006 Marcotte et al.
2006/0184040 A1 8/2006 Keller et al.
2006/0206027 A1 9/2006 Malone

(56) References Cited

U.S. PATENT DOCUMENTS

| | | | |
|---|---|---|---|
| 2006/0232660 | A1 | 10/2006 | Nakajima et al. |
| 2006/0253010 | A1 | 11/2006 | Brady et al. |
| 2006/0271028 | A1 | 11/2006 | Altshuler et al. |
| 2006/0276712 | A1 | 12/2006 | Slothers |
| 2007/0015980 | A1 | 1/2007 | Numada et al. |
| 2007/0016079 | A1 | 1/2007 | Freeman et al. |
| 2007/0070302 | A1 | 3/2007 | Govorkov et al. |
| 2007/0115435 | A1 | 5/2007 | Rosendaal |
| 2007/0129634 | A1 | 6/2007 | Hickey et al. |
| 2007/0176851 | A1 | 8/2007 | Willey et al. |
| 2007/0232923 | A1 | 10/2007 | Asuri |
| 2007/0238995 | A1 | 10/2007 | Yared |
| 2008/0045841 | A1 | 2/2008 | Wood et al. |
| 2008/0086533 | A1 | 4/2008 | Neuhauser |
| 2008/0147147 | A1 | 6/2008 | Griffiths et al. |
| 2008/0194930 | A1 | 8/2008 | Harris et al. |
| 2008/0214940 | A1 | 9/2008 | Benaron |
| 2009/0018414 | A1 | 1/2009 | Toofan |
| 2009/0082629 | A1 | 3/2009 | Dotan |
| 2009/0171205 | A1 | 7/2009 | Kharin et al. |
| 2010/0051808 | A1 | 3/2010 | Zeman et al. |
| 2010/0061598 | A1 | 3/2010 | Seo |
| 2010/0087787 | A1 | 4/2010 | Woehr et al. |
| 2010/0177184 | A1 | 7/2010 | Berryhill et al. |
| 2011/0021925 | A1 | 1/2011 | Wood et al. |
| 2011/0275932 | A1 | 11/2011 | Leblond et al. |
| 2013/0147916 | A1 | 6/2013 | Bennett et al. |
| 2014/0039309 | A1 | 2/2014 | Harris et al. |
| 2014/0046291 | A1 | 2/2014 | Harris et al. |
| 2014/0194747 | A1 | 7/2014 | Kruglick |

FOREIGN PATENT DOCUMENTS

| | | | |
|---|---|---|---|
| JP | S60-108043 | A | 6/1985 |
| JP | 04-042944 | | 2/1992 |
| JP | 07-255847 | | 10/1995 |
| JP | 08-023501 | A | 1/1996 |
| JP | 08-164123 | | 6/1996 |
| JP | 2000-316866 | A | 11/2000 |
| JP | 2002-328428 | A | 11/2002 |
| JP | 2002-345953 | A | 12/2002 |
| JP | 2004-237051 | | 8/2004 |
| JP | 2004-329786 | A | 11/2004 |
| JP | 2006-102360 | A | 4/2006 |
| KR | 2003-0020152 | A | 3/2003 |
| WO | 1994-22370 | | 10/1994 |
| WO | 1996-39925 | | 12/1996 |
| WO | 1998-26583 | | 6/1998 |
| WO | 1999-48420 | | 9/1999 |
| WO | 2001-82786 | | 11/2001 |
| WO | 2003-009750 | | 2/2003 |
| WO | 2005-053773 | | 6/2005 |
| WO | 2007-078447 | | 7/2007 |

OTHER PUBLICATIONS

Nikbin, Darius, “IPMS Targets Colour Laser Projectors”, Optics & Laser Europe, March 1006, Issue 137, p. 11.

http://sciencegeekgirl.wordpress.com/category/science-myths/page/2/ Myth 7: Blood is Blue.

http://www.exploratorium.edu/sports/hnds_up/hands6.html “Hands UP! To Do & Notice: Getting the Feel of Your Hand”.

http://www.wikihow.com/See-Block-Veins-in-Your-Hand-With-a-Flashlight “How to See Blood Veins in Your Hand with a Flashlight”.

Alpha Blended Projection
38
Fused Vein Projection
36
Alpha Channel
37
Vein Processing
33T
Exposure Control
35
Vein Processing
33B
Histogram
32T
Mirror Convergence Control
34
Histogram
32B
Top Channel Data
30T
Line Correlator
31T
Line Correlator
31B
Bottom Channel Data
30B Vein Algo Architecture 2-D Moving Window Sum Generator Latency = X-Sum Buffer Size + Y-Sum Buffer Size X-Sum Buffer Size = (boxsize - 1)*(number_of_horizontal_pixels) ;
Y-Sum Buffer Size = (boxsize - 1);

X-sum generator (Boxsize – 1) stage shift register

DEVICE FOR DETECTING AND ILLUMINATING THE VASCULATURE USING AN FPGA

CROSS-REFERENCE TO RELATED APPLICATIONS

This application is a continuation of U.S. patent application Ser. No. 17/991,924, filed on Nov. 22, 2022, which is a continuation of U.S. patent application Ser. No. 16/789,459, filed on Feb. 13, 2020, which issued as U.S. Pat. No. 11,510,617 on Nov. 29, 2022, which is a continuation of U.S. patent application Ser. No. 15/679,277, filed on Aug. 17, 2017, which issued as U.S. Pat. No. 10,568,518 on Feb. 5, 2020, which is a continuation of U.S. patent application Ser. No. 14/723,674, filed on May 28, 2015, which issued as U.S. Pat. No. 9,782,079 on Oct. 10, 2017, which is a continuation of U.S. patent application Ser. No. 13/957,767, filed on Aug. 2, 2013, which issued as U.S. Pat. No. 9,072,426 on Jul. 7, 2015, which claims priority on U.S. Provisional Patent Application Ser. No. 61/678,726, filed on Aug. 2, 2012, with the disclosures of each being incorporated herein by reference.

BACKGROUND

Summary

A laser based vascular illumination system utilizing a FPGA for detecting vascular positions, processing an image of such vasculature positions, and projecting the image thereof onto the body of a patient.

BRIEF DESCRIPTION

FIG. 1 Block diagram of a system for detecting and illuminating the vasculature in a patient.

Figure 2:
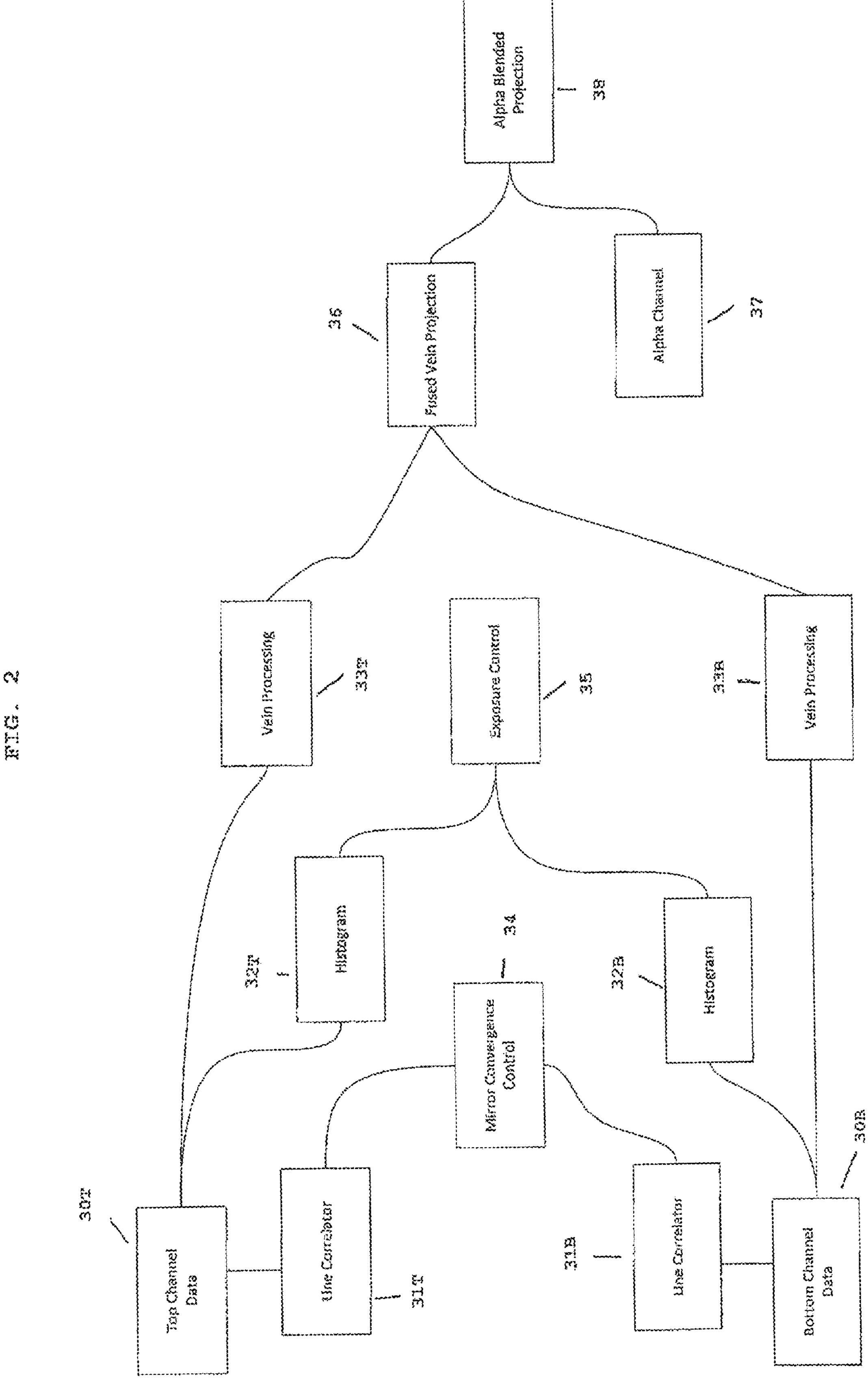
FIG. 2 Shows the signal processing flow of the FPGA.
Figure 7:
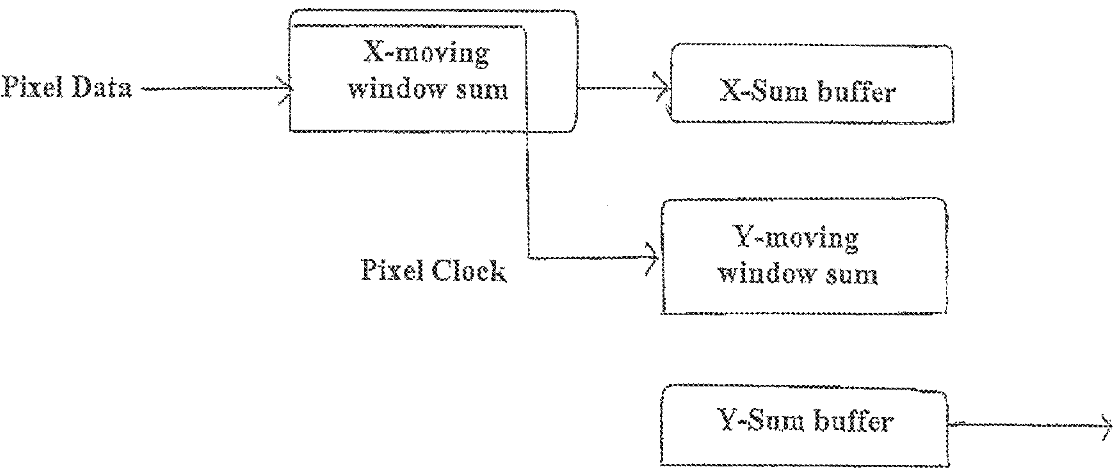

FIG. 7 2-D Moving Window Sum Generator.

Figure 8:
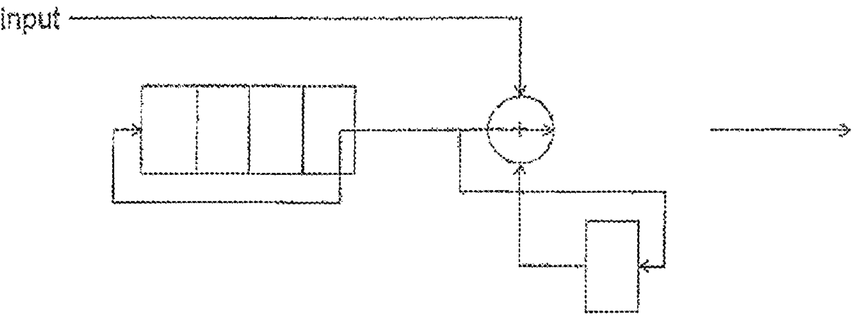

FIG. 8 shows a X-sum generator.

DETAILED DESCRIPTION

Figure 1:
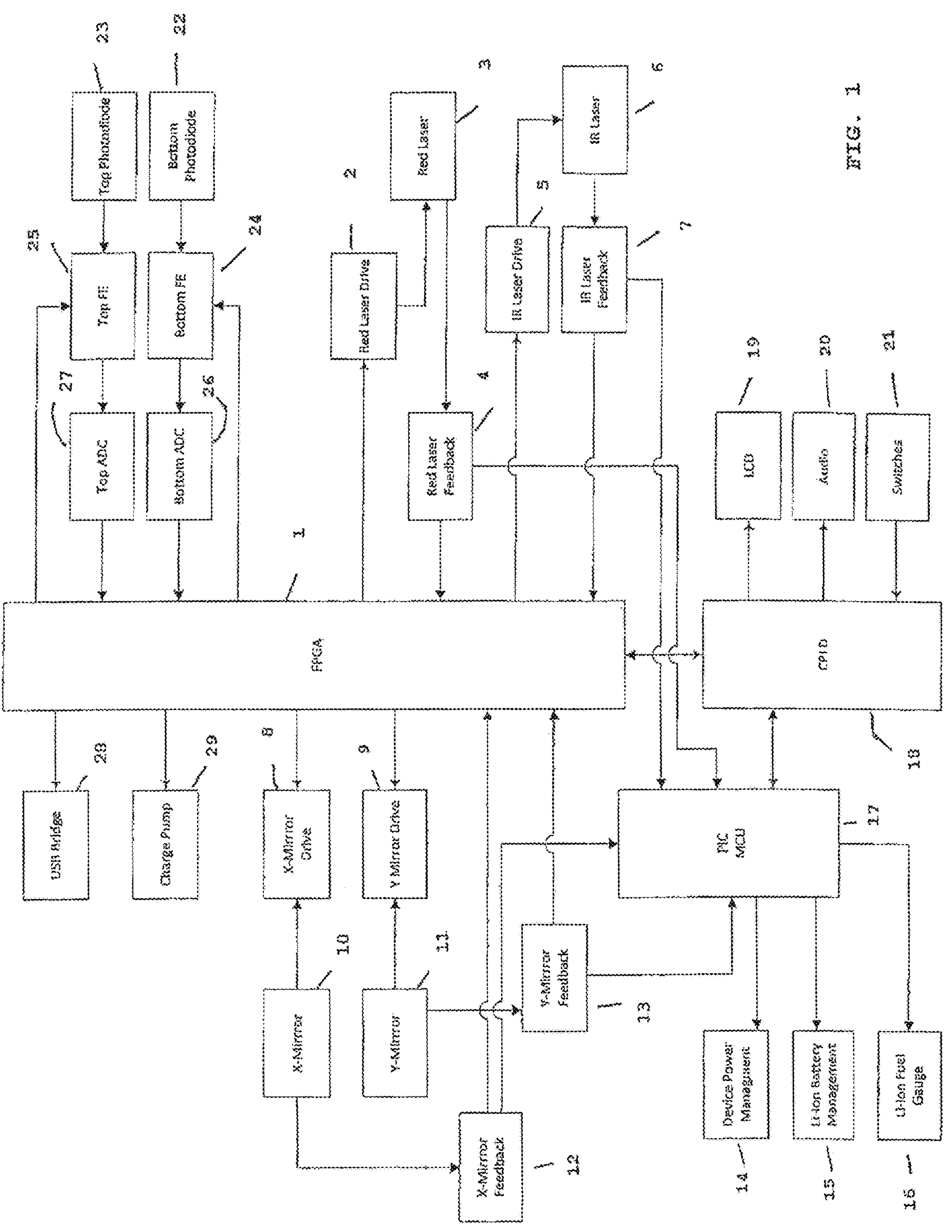

FIG. 1 shows a block diagram of a system for detecting and illuminating the vasculature in a patient.

The system shown in the block diagram of FIG. 1 is used for detecting the location of veins on a patient and illuminating the veins.

The disclosures of U.S. patent application Ser. No. 12/804,506, now issued as U.S. Pat. No. 8,463,364 are incorporated herein by reference.

In a preferred embodiment, FIGS. 30-47 of application Ser. No. 12/804,506 illustrates an assembly of a housing that may be used in the present invention. In the present invention, circuit boards 43, 44 and 15 of application Ser. No. 12/804,506 may be modified to contain the circuitry described by the block diagram in FIG. 1. The remainder of the device in FIGS. 30-47 can remain substantially the same.

In FIG. 1 an FPGA 1 (field programmable gate array) is configured to control a red laser drive 2 which in turn drives a red laser 3. The output of the red laser 3 is controlled in a manner so as to illuminate the detected veins. A red laser feedback 4 detects the output of the red laser 3 and sends the information to the FPGA 1. Accordingly, a closed loop is formed whereby the FPGA 1 can both drive the Red laser 3 and receive feedback as to the red laser 3 state.

In FIG. 1 an FPGA 1 (field programmable gate array) is configured to control a red laser drive 2 which in turn drives a red laser 3. The output of the red laser 3 is controlled in a manner so as to illuminate the detected veins. A red laser feedback 4 detects the output of the red laser 3 and sends the information to the FPGA 1. Accordingly, a closed loop is formed whereby the FPGA 1 can both drive the Red laser 3 and receive feedback as to the red laser 3 state.

FPGA 1 outputs data to an IR laser drive 5 which in turn drives an IR laser 6. The output of the IR laser 6 is controlled to output an intensity of IR light, aimed at the area of the body where veins are located, sufficient to detect the veins. An IR laser feedback 7 detects the output of the IR laser 6 and sends the information to the FPGA 1. Accordingly, a closed loop is formed whereby the FPGA 1 can both drive the IR Laser 6 and receive feedback as to the IR laser 6 state.

FPGA 1 communicates to both a x-mirror drive 8 and a y-mirror drive 9 to drive x-mirror 10 and y-mirror 11 in such a manner that a raster pattern is formed on the patient when the Red laser 3 and the IR laser 6 are coaxially projected thereon. X-mirror feedback 12 and y-mirror feedback 13 detect the positions of the x-mirror 10 and y-mirror 11, respectively, and communicates such information to the FPGA1.

Top photodiode 23 and bottom photodiode 22 receive the IR Laser 6 reflected off the patient, converts the light into an analog signal which is provided to Top FE 25 and Bottom FE 24, and then to Top ADC 27 and bottom ADC 25, respectively. The top FE 25 and the bottom FE 24 are front end circuits that provide analog filtering, gain control and threshold of the analog signals. The Top ADC 27 and bottom ADC 26 are analog to digital converters that convert the analog signals to digital representations thereof to be communicated to the FPGA 1. Control lines are provided from the FPGA 1 to the top FE 25 and the bottom FE 24 to set parameters such as, for example, gain control and analog filtering.

From a mechanical standpoint, the red laser 3 and the IR laser 6 are co axially aligned and projected off of mirrors X-mirror 10 and Y-mirror 11 to form a pattern, such as for example, a raster pattern on the patient. The IR laser 6 reflects off the patient and is received by top photodiode 23 and photodiode 22. The reflected IR light contains information as to the location of the veins (IR light is absorbed by the blood in the veins and therefore the amount or reflected IR light is lower when the IR laser 6 is aimed at a vein. The FPGA 1 time sequentially receives in the signal form the top ADC 27 and the bottom ADC and can form two partial and/or full frame images of the reflected IR light (hereinafter a top channel data and a bottom channel data wherein the top channel data is received from the top ADC 27 and the bottom channel data is received from the bottom ADC). The FPGA 1 processes one or both of the partial and/or full image to detect and enhance the image of the veins. The enhanced image is time sequentially projected by the Red laser 3 onto the patient.

A CPLD is provided for controlling an LCD 19 with displays user information related to the operating status of the device. It also controls an audio 20 output to provide audible tones to the user. Finally the CPLD 18 controls the switches 21 on the unit for turning on and off the units as well as selecting user modes and entering data.

A microprocessor PIC MCU 17 is provided for receiving and monitoring the IR laser feedback 7 signal, the red laser feedback 4 signal, the x-mirror feedback 12 signal and the y-mirror feedback 13 signal. Since these signals are also provided to the FPGA 1, redundancy monitoring of the signals is provided by the PIC MCU 17. This is particularly important when regulatory requirements require redundant monitoring of the laser power and movement to comply with safety requirements. The NC MCU 17 also monitors the device power management 14, the Li-ion Battery management 15 circuitry and the Li-ion Fuel gauge 16.

FIG. 2 Shows an example of the signal processing flow of the FPGA.

FIG. 2 shows an embodiment of the signal processing algorithm of the FPGA of FIG. 1. As described with reference to FIG. 1, the image of the reflected IR laser 6 is time sequentially stored in the FPGA 1 as top channel data 30T and bottom channel data 30B.

The X-mirror 10 oscillates about a single axis to move the laser beam from the IR laser 6 to form a line. The beam moves first in one direction and then back in the other direction. It is critical that the left to right image data be in convergence with the right to left data. The top line correlator 31T measures the shift in the convergence of the top channel data 30T and supplies the information to the mirror convergence control 34. Similarly, the bottom line correlator 31B measures the shift in the convergence of the bottom channel data 30B and supplies the information to the mirror convergence control 34. The mirror convergence control 34 can adjust the control signals provided from the FPGA 1 to the x-mirror drive 8 so as to converge the data.

A top histogram 32T receives the top channel data 30T and generates a histogram based upon an entire frame of the top channel data 30T. Similarly, a bottom histogram 32B receives the top channel data 30B and generates a histogram based upon an entire frame of the bottom channel data 30B. The histograms contain information describing the characteristics of the images, including but not limited to contrast and intensity levels. The top histogram 32T and the bottom histogram 32B are provided to exposure control 35. Exposure control 35 communicates appropriate signals the IR laser drive 5 to adjust the power of the IR laser 6 on a frame by frame basis until the histograms indicate appropriate images. The exposure control 35 also communicates with the top FE 25 and bottom FE 24 to adjust parameters such as setting thresholds and setting electrical gain.

A top vein processing 33T block receives the top channel data 30T and performs image processing to detect vein patterns and provides the enhanced vein image to fused vein projection 36. Similarly, bottom vein processing 33B block receives the bottom channel data 30B and performs image processing to detect vein patterns and provides the enhanced vein image to fused vein projection 36. The fused vein projection 36 forms a single image and communicates the Image to the alpha blended projection 38. The fused vein projection 36 can form the single image by merging the images from the top vein processing 33T and bottom vein processing 33B. Alternative, the fused vein projection 36 can simply select the best image received from the top vein processing 33T and the bottom vein processing 33B.

Alpha channel 37 forms an image that contains graphical data, such as text or characters. Alpha channel 37 and fused vein projection 36 are provided to alpha blended projection 38 with drives the IR laser drive 5 to display an image which is the combination of the fused vein projection 36 and the alpha channel 37.

Figure 3:
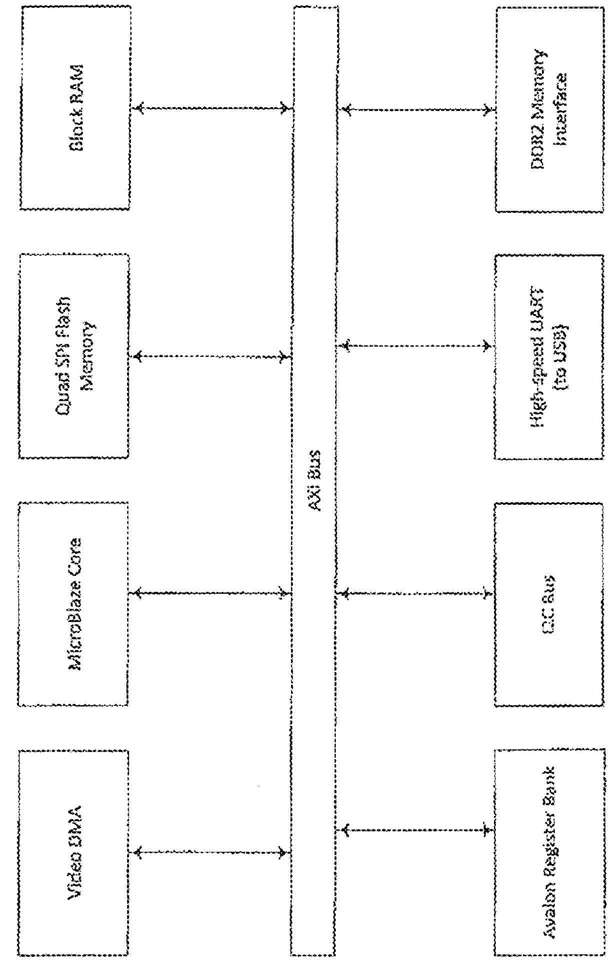
FIG. 3 shows the internal bus architecture of the FPGA.

FIG. 3 shows an example of the internal bus architecture of the FPGA.

Figure 4:
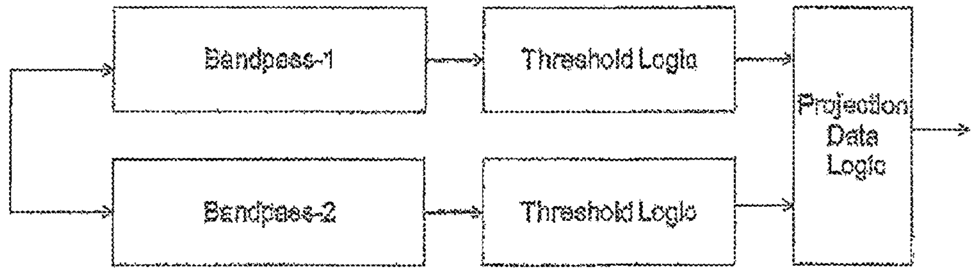
FIG. 4 shows details of the vein processing.

FIG. 4 shows details of the top vein processing 33T and bottom vein processing 33B.

Figure 5:
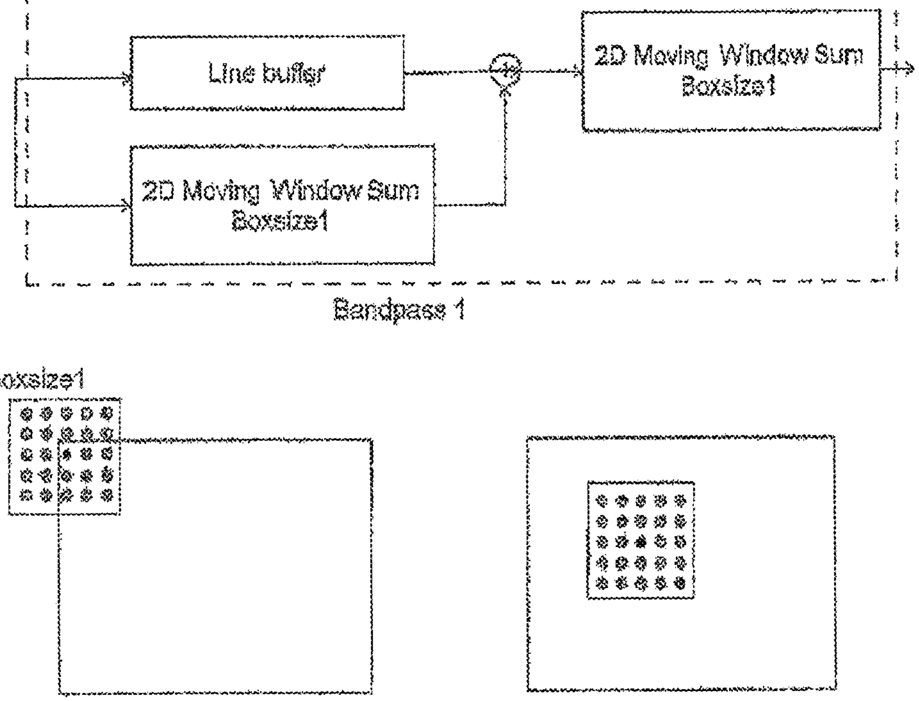
FIG. 5 shows the vein processing at the boundary of the image frames.

FIG. 5 shows the vein processing at the boundary of the image frames.

Figure 6:
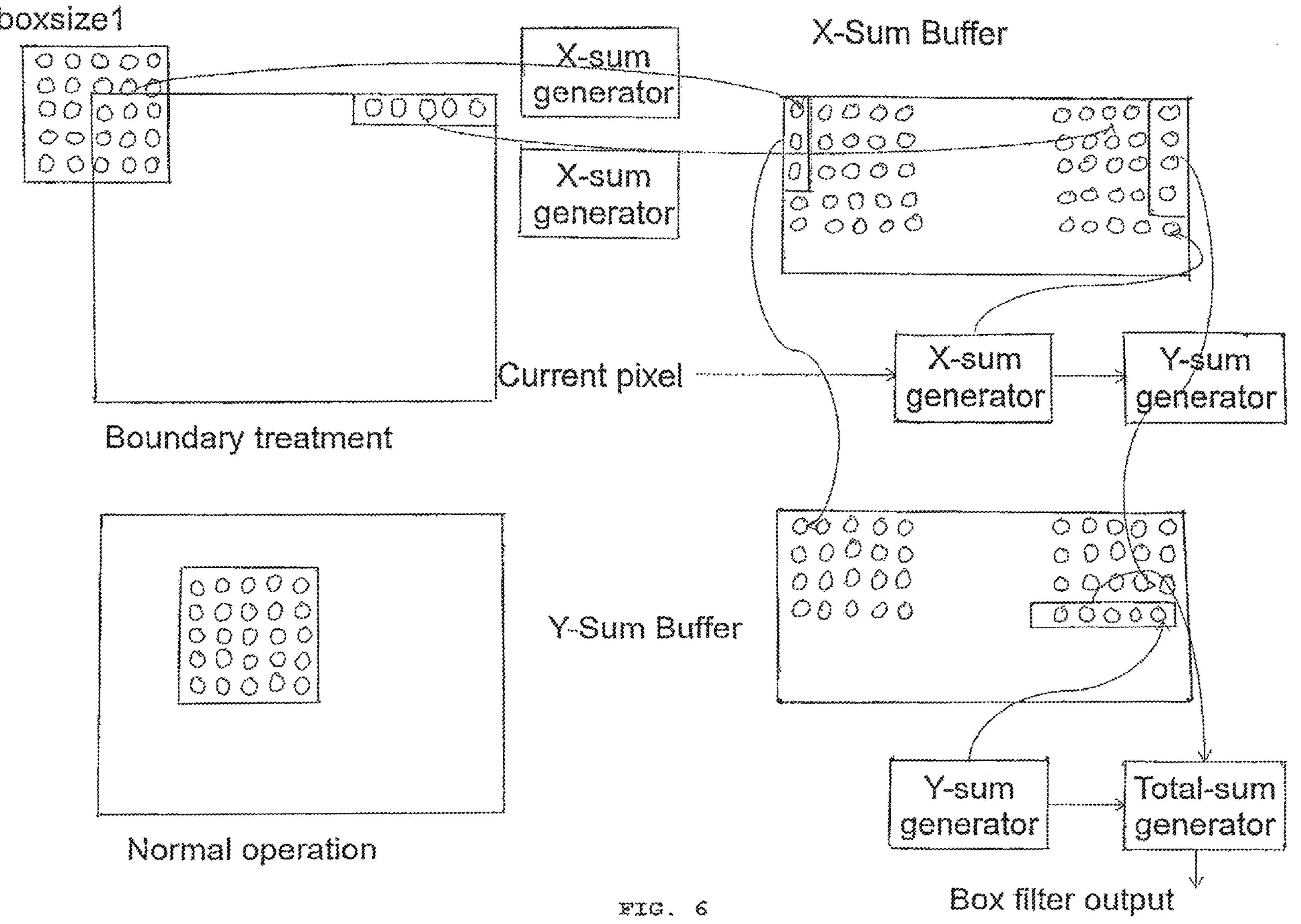
FIG. 6 shows further detail of the vein processing at the boundary of the image frames.

FIG. 6 shows further detail of the vein processing at the boundary of the image frames.

FIG. 7 shows the 2-D Moving Window Sum Generator.

FIG. 8 shows a X-sum generator.

The invention claimed is:

1. A vein imaging device configured to obtain and project an image of subcutaneous veins onto a patient to overlie the imaged veins, said vein imaging device comprising:

a first laser configured to emit a beam of light at an infrared wavelength;

a second laser configured to emit a beam of light at a visible wavelength;

an x-mirror;

an x-mirror driver;

a y-mirror;

a y-mirror driver;

a field programmable gate array (FPGA), said FPGA configured to control said x-mirror driver and said y-mirror driver to control said first laser, said second laser, said x-mirror and said y-mirror to selectively scan each of said beam of light at said infrared wavelength and said beam of light at said visible wavelength onto the patient in a first direction and then in a second direction, to form lines, and to scan said lines in a third direction to thereby form a pattern of said infrared wavelength of light and said visible wavelength of light;

wherein said FPGA is further configured to receive feedback of a state of said first laser and a state of said second laser, to form a closed loop to control an output of said first laser and to control an output of said second laser;

a photodiode configured to receive a vein image formed from said scanned pattern of said infrared wavelength of light, and further configured to convert the received vein image into an analog signal;

a front end circuit, said front end circuit configured to provide analog filtering, gain control, and threshold of the analog signal;

an analog to digital converter (ADC), said ADC configured to convert the analog signal to a digital signal;

wherein said FPGA is further configured to receive the digital signal and to perform vein image processing of an image frame of said received vein image, said vein image processing comprising: said FPGA being configured to collect pixel data from said photodiode, to perform an X-direction sum of pixel data for a plurality of boundary windows comprising: a matrix of pixels, and to place said X-direction sum into an X-sum buffer, to perform a Y-direction sum of pixel data for said plurality of boundary windows, and to place said Y-direction sum into a Y-sum buffer, and to use a total sum generator to obtain box filter output for each of said plurality of windows being the X-sum buffer added to the Y-sum buffer;

wherein said FPGA is further configured to control said x-mirror driver and said y-mirror driver to control said first laser, said second laser, said x-mirror and said y-mirror, to scan said visible wavelength within said beam for projection of said processed vein image onto the patient; and wherein said FPGA is further configured to set said analog filtering and gain, to control said front end circuit.

2. The imaging device according to claim 1, wherein said FPGA is further configured to provide boundary treatment image processing, wherein a portion of one or more of said plurality of boundary windows extend beyond said image frame.

3. The imaging device according to claim 2, further comprising a pixel clock configured to time sequentially store said image in said FPGA.

4. The imaging device according to claim 1, further comprising: a pixel clock.

* * * * *